(12) United States Patent
Williams

(10) Patent No.: US 7,025,718 B2
(45) Date of Patent: Apr. 11, 2006

(54) METHOD AND DEVICE FOR CORRECTING IN-VIVO SENSOR DRIFT

(76) Inventor: Jonathan Williams, 28 Macleay Rd., Montville, NJ (US) 07045

( * ) Notice: Subject to any disclaimer, the term of this patent is extended or adjusted under 35 U.S.C. 154(b) by 655 days.

(21) Appl. No.: 10/299,369

(22) Filed: Nov. 19, 2002

(65) Prior Publication Data
US 2004/0097813 A1 May 20, 2004

(51) Int. Cl.
*A61N 1/362* (2006.01)
(52) U.S. Cl. .................... 600/18; 600/485; 702/98; 702/189
(58) Field of Classification Search ............ 600/18, 600/485, 486; 702/104, 106, 69, 70, 190, 702/191, 98
See application file for complete search history.

(56) References Cited

U.S. PATENT DOCUMENTS

| 3,585,983 A | 6/1971 | Kantrowitz |
| 4,733,652 A | 3/1988 | Kantrowitz et al. |
| 5,158,529 A | 10/1992 | Kanai et al. |
| 5,169,379 A | 12/1992 | Freed et al. |
| 5,431,628 A | 7/1995 | Millar |
| 5,902,248 A | 5/1999 | Millar et al. |
| 6,245,008 B1 | 6/2001 | Leschinsky et al. |
| 6,398,738 B1 | 6/2002 | Millar |

*Primary Examiner*—Robert E. Pezzuto
*Assistant Examiner*—Eric Bertram
(74) *Attorney, Agent, or Firm*—J. Gary Mohr

(57) ABSTRACT

A method and device for reducing signal drift on a balloon catheter mounted pressure sensor by adjusting for signal gain and/or zero offset, and by separately calibrating the constant signal component and the time-varying signal component of an uncalibrated source signal to produce a calibrated source signal.

21 Claims, 13 Drawing Sheets

METHOD AND DEVICE FOR CORRECTING IN-VIVO SENSOR DRIFT

BACKGROUND OF THE INVENTION

1. Field of the Invention

The invention relates to an intra-aortic balloon pump system. More particularly, the invention relates to a method and device for accurately measuring arterial blood pressure via a pressure sensor on an intra-aortic balloon catheter.

2. Description of the Prior Art

A key function of many catheters is that of continuously monitoring blood pressure. In many cases, this process must provide accurate measurement of the blood pressure waveform's high frequency components. For example, reliable detection of the dicrotic notch of the aortic blood pressure waveform typically requires a pressure signal having a bandwidth of 15 Hz or better. Detection of the dicrotic notch is generally used for the inflation/deflation timing of an intra-aortic balloon ("IAB") catheter.

Conventional IAB catheter invasive pressure monitoring is performed with low cost piezo resistive transducers, which are hydraulically coupled to the targeted monitoring site in the patient. Typically, the tip of the IAB is hydraulically coupled to a transducer external to the patient's body.

The chief benefit of the current configuration is its low cost. The typical disposable monitoring kit, inclusive of all tubing, a continuous flush device, and a pre-calibrated transducer is very affordable.

Unfortunately, hydraulically coupled transducers are vulnerable to motion artifact. Inflation and deflation of the IAB balloon membrane causes movement of the IAB catheter, which generates inertial forces in the fluid and pressure transducer coupled to it, resulting in artifact. Patient movement can cause a similar result. Therefore, a waveform may contain artifact in the form of "overdamping", "ringing", and "catheter whip".

Another disadvantage of the traditional transducer configuration is that it requires the use of a separate inner lumen to couple the transducer to the tip of the IAB catheter. Traditionally, IAB catheters have two lumens in the catheter: a gas shuttle lumen and an inner guidewire lumen. The gas shuttle lumen has to be large enough to allow the gas to shuttle back and forth without undue restriction to ensure rapid inflation and deflation of the IAB membrane. The guidewire lumen serves two functions: It hosts the guidewire for IAB placement and, once the IAB is placed and the guidewire is removed, it is used for pressure monitoring. When the guidewire lumen is present, it reduces the cross-sectional area available for shuttle gas flow and, hence, it indirectly slows IAB inflation and deflation. Therefore, it is desirable to eliminate the guidewire lumen altogether. Elimination of the guidewire lumen creates a need for an alternate means for measuring arterial pressure.

One alternate means for monitoring blood pressure involves the use of a fiber optic sensor as disclosed in U.S. patent application Ser. Nos. 09/734,755 and 09/925,143, filed on Dec. 11, 2000 and Aug. 9, 2001, respectively, and assigned to Datascope Investment Corp., herein incorporated by reference in their entirety.

Alternatively one can use a micromanometer on the tip of the IAB, such as marketed by companies such as Millar, Endosonics, and Radi. See U.S. Pat. Nos. 5,431,628, 5,902,248 and 6,398,738, all herein incorporated by reference. These devices have an excellent frequency response, with system bandwidths greater that 200 Hz. They are not subject to the negative effects of hydraulic coupling, such as motion artifact, air bubbles, and catheter whip. Also, they retain good performance in the presence of small blood clots. Attempts have been made to use micro-manometers for IAB pump timing, see U.S. Pat. Nos. 3,585,983 and 4,733,652, herein incorporated by reference. These attempts have proven to be unsuccessful because the device is prone to signal drift and is susceptible to interference from electro-surgical units.

Unfortunately, both micro-manometers and fiber optic sensors are prone to the problem of signal drift. Many different physical phenomena may cause drift. Changes in the apparent zero offset can occur with any hydraulically coupled pressure sensor simply as a result of changes in the relative heights of the sensor and the point of measurement in the patient. This is a direct result of the hydrostatic pressure exerted by the fluid-filled line upon the sensor, i.e. the "hydraulic head". In normal practice, care is taken to assure that the point of measurement (such as the patient's right atrium) is at the same level as the pressure sensor.

Drift can also occur as a result of changes within the sensor itself. A typical sensor construction employs a deformable diaphragm which has one side exposed to the medium being measured and the other side exposed to a known reference pressure. This construction is commonly used for various sensor designs, including electronic and fiber optic sensors. In the electronic sensor, the diaphragm's deformation is sensed by measurement of changes in the electrical characteristics of an electrical circuit, which is mechanically coupled to the diaphragm. In the fiber optic sensor, the diaphragm's deformation is sensed optically by fiberoptically-transmitted light, which is retro-reflected by a surface of the diaphragm. In any case, if the reference pressure changes, the apparent pressure as indicated by the sensor will change as well.

In one specific application of the above design approaches, a sealed reference chamber faces the diaphragm. This chamber encloses a small volume of gas, which is at atmospheric pressure at the time of sensor fabrication. The pressure of this gas-filled chamber is the reference pressure. Zero drift, also known as offset, can occur as the temperature of the sensor changes; the gas will either expand as it is warmed, or contract as it is cooled. The zero drift will occur as a result of the consequent change in the diaphragm position.

In another specific application of the above design approaches, the reference pressure is a vacuum (zero pressure), which is maintained in the reference chamber. This construction is less resistant to temperature induced zero drift changes than the previous example, since there is no gas within the chamber to expand or contract.

The sensor's offset can also drift due to various other factors, such as repetitive stress, moisture absorption, chemical reactions, mechanical fatigue, aging, micro-structural changes or temperature-induced stress.

For both of the above constructions, as well as for others, drift in the transducer's scale factor (gain) can also occur. This can be the result of a change in stiffness of the diaphragm, which can occur due to various factors, such as repetitive stress, moisture absorption, chemical reactions, aging, micro-structural changes or temperature changes. In addition, the adhesive bonds which couple the diaphragm to the reference chamber may result in a change in stiffness, causing a change in the sensitivity of the device to pressure. Finally, the interface electronics, which convert the optical signal to an electrical signal can be prone to both gain and offset drift.

To address the offset drift issue, U.S. Pat. No. 5,158,529, issued to Kanai, discloses a method for re-zeroing the micromanometer by using the pressure from a partially filled balloon as it rests in the aorta. The Kanai method for addressing the problem of drift has a significant disadvantage. Namely, Kanai attempts to correct for offset at a defacto calibration point at mean blood pressure, and thus, does not completely eliminate the drift error. Furthermore, Kanai completely ignores the gain shift problem, which may also significantly contribute to signal drift and results in a loss of accuracy.

Kanai's method for reducing zero point drift is also faulty because an inaccurate method is used to compute mean pressure. Kanai's computation uses the peak and valley of the shuttle gas pressure waveform. These features are likely to be corrupted when they are measured, via the IAB membrane, by the shuttle gas transducer. Further, the formulation used by Kanai is a crude approximation; it only valid for saw-tooth shaped pressure waveforms.

U.S. Pat. No. 6,398,738, issued to Millar, discloses a method and system for reconstructing a high-fidelity pressure waveform with a balloon catheter used in a heart. The AC components of the aortic pressure and the mean aortic pressure are detected separately and then added to form a high-fidelity pressure waveform. The AC components are detected by a catheter based pressure sensor. The mean pressure within the balloon is detected by an external pressure sensor.

The Millar device suffers from a number of drawbacks. Firstly, Millar does not correct for errors in the micromanometer's gain or drift in gain. In Millar's configuration, the micro-manometer's signal is AC coupled. This signal is used as the source for the amplitude of the AC components of the physiologic signal. If the gain is not corrected, then the amplitude of the displayed pulse will be in error.

Further, Millar uses a separate source for the patient's mean pressure, i.e. the "DC component", of the blood pressure waveform. The AC and DC signals are summed to yield a composite pressure waveform. The fidelity of the pressure waveform can be corrupted if the filters or methods used to extract the AC signals from the micromanometer and the DC (mean pressure) signal from the secondary source are not coordinated.

In Millar, the "DC signal" is "extracted" from a secondary external pressure transducer and the AC component is extracted by "capacitive coupling". The capacitor implicitly interacts with other impedances, such as the micro-manometer's resistive bridge to form a "defacto" high pass filter. This filter has a "break frequency", a frequency at which higher frequencies are passed without significant attenuation. Lower frequencies are attenuated in proportion to their distance from the break frequency. The details of the extraction process are not disclosed. However, Millar requires that the process extract only the mean pressure. This implicitly means that all other AC components are eliminated from the "DC" signal. When this signal is then summed with the AC coupled signal from the micromanometer, it is missing some of the original signal content. Specifically, it is missing the attenuated signals that existed below high pass filter's break frequency. As a consequence of this omission, the displayed waveform is distorted.

While the Kanai zeroing method for reducing signal drift or the Millar high-fidelity reconstruction may be suitable for the particular purpose employed, or for general use, they would not be as suitable for the purposes of the present invention as disclosed hereafter.

SUMMARY OF THE INVENTION

The invention is a method and device for calibrating a balloon catheter mounted pressure sensor by correcting for its signal gain error and zero offset error. The catheter pressure sensor is used to monitor patient's aortic blood pressure during TAB therapy. The catheter sensor may be implemented via use of a fiber optic sensor, or via use of a micromanometer, or via their equivalent.

The calibration process uses simultaneous measurements from the catheter sensor and from a reference source. In one embodiment, this reference measurement is extracted from a measurement of shuttle pressure, under a range specific conditions of IAB inflation. The details of the necessary conditions are disclosed.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

The details of the invention are explained below as used with an intra-aortic balloon (IAB) catheter system. However, the present invention may be used to remedy the signal drift problem with any catheter-based system having an in-dwelling sensor of any kind and a second source for calibrated measurement.

It is well known in the art, as described in, for example, the specification of U.S. Pat. No. 4,362,150, to provide cardiac assistance by introducing a balloon into the thoracic aorta of a patient and causing the balloon to inflate and deflate in anti-phase with the contraction of the patient's heart. A balloon of this type is inflated at the beginning of diastole, in order to increase the blood flow to the coronary and carotid arteries. The balloon is then deflated just prior to the start of systole, in order to reduce the load on the left ventricle. IAB therapy increases coronary artery perfusion, decreases the workload of the left ventricle, and allows healing of the injured myocardium. It is essential that cardiac activity be sensed reliably to ensure that the balloon is inflated and deflated accurately with respect to the cardiac cycle. It is also important to present accurate blood pressure values to the physicians treating the patient.

Methods of sensing cardiac activity include analysis of aortic pressure and/or analysis of the electrocardiogram. It is known in the art, as described in U.S. Pat. No. 5,169,379, to combine means for effecting such analysis with the aforementioned intra-aortic balloon (IAB) apparatus.

Figure 1:
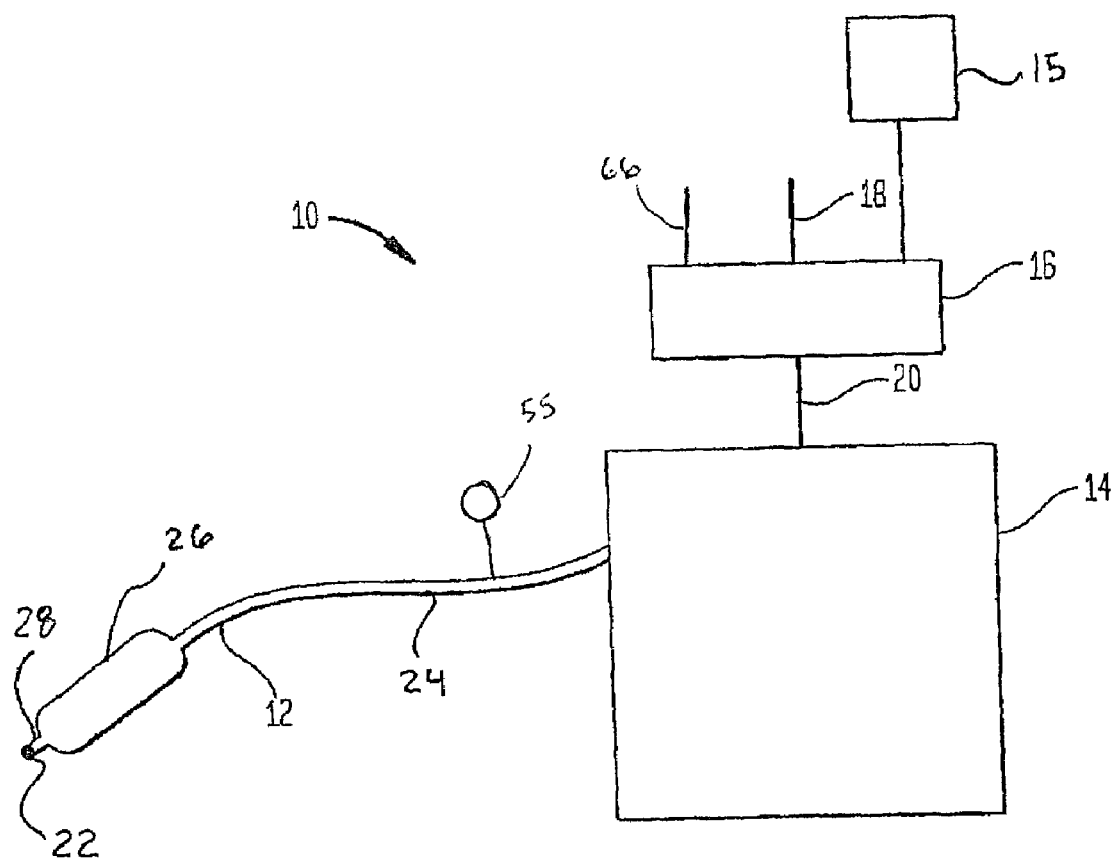
FIG. 1 is a block diagram of an intra-aortic balloon catheter pump system.

FIG. 1 illustrates an intra-aortic balloon pump (IABP) system 10 comprising an intra-aortic balloon catheter 12, a pneumatic drive module 14, a display 15, and a control logic module 16. IAB catheter 12, for insertion into a blood vessel of a patient (not shown), is connected to the pneumatic drive module 14. The pneumatic drive module 14 is in communication with the control logic module 16 via an inflate/deflate control line 20. Pressure sensor 55, continuously measures the pressure of shuttle gas in the IAB shuttle gas pneumatic circuit and communicates with control logic module 16.

Display 15 is connected to control logic module 16 and is used to display parameters such as a patient's blood pressure waveform, blood pressure values (diastolic, mean, systolic, and augmented), electrocardiogram, heart rate, timing settings, and balloon gas pressure. See U.S. Pat. No. 6,245,008, herein incorporate by reference in its entirety, for details regarding pneumatic drive modules for IABs. Note that display 15 and control logic module 16 may be incorporated with pneumatic drive module 14 to form a single unit.

IAB catheter 12 comprises a tube 24 connected on a distal end to a proximal end of a balloon membrane 26. A distal end of the balloon membrane is connected to a tip 28 containing a pressure sensor 22. Pressure sensor 22 measures the patient's aortic blood pressure, ideally with sufficient fidelity to resolve key hemodynamic features of the aortic pressure waveform.

Pressure sensor 22 may be connected to IAB catheter 12 at other locations along its length; however, connection to tip 28 is preferred. Pressure sensor may be embedded in an outside surface of tip 28 or such that it is exposed to a lumen inside tip 28. See U.S. patent application Ser. Nos. 09/735,076, 09/734,755 and 09/925,143, filed on Dec. 11, 2000, Dec. 11, 2000 and Aug. 9, 2001, respectively, herein incorporated by reference in their entirety, for details concerning the various means for connecting pressure sensor 22 to tip 28 and for details regarding the alternate constructions and embodiments of IAB catheter 12. IAB catheter 12 may comprise an outer tube and an optional inner tube disposed within the outer tube. The inner tube may extend the length of catheter 12 to tip 28 and be coaxial with the outer tube, connected to an inner surface of the outer tube or embedded in the wall of the outer tube.

Catheter pressure sensor 22 may comprise any pressure sensing means, including, but not limited to piezoresistive, piezoelectric and piezoacoustic based devices, as well as a fiber optic sensor device as disclosed in U.S. patent application Ser. Nos. 09/734,755 and 09/925,143, filed on Dec. 11, 2000 and Aug. 9, 2001, respectively, herein incorporated by reference in their entirety. Catheter pressure sensor 22 may also comprise a micromanometer, such as marketed by companies such as Millar, Endosonics, and Radi. See U.S. Pat. Nos. 5,431,628 and 5,902,248, herein incorporated by reference.

A stylet (not shown) may extend from a distal end of catheter 12 to tip 28 and may have a "monorail" tip, as disclosed in U.S. patent application Ser. No. 10/091073, filed on Mar. 5, 2002, herein incorporated by reference in its entirety. The stylet may optionally vary in diameter along its length.

Control logic module 16 has pressure input line (not shown) from pressure sensor 22, an ECG input line 18 and may also have an inflation and deflation adjustment control line (not shown). Control logic module 16 uses information communicated via the pressure sensor line, the ECG input line 18, in conjunction with an inflation and deflation adjustment control, to determine when to output an inflate signal or a deflate signal to pneumatic drive module 14 via inflate/deflate line 20. Upon command from control logic module 16, pneumatic drive module 14 inflates or deflates balloon membrane 26. The pressure of the shuttle gas used to inflate and deflate the IAB is monitored by pressure sensor 55. This sensor communicates with a control logic module 16.

In some cases, an external measurement of patient blood pressure is available, e.g. a measurement from a bedside monitor. This signal is supplied to IABP control logic module 16 via External AP Input 66.

Control logic module 16 also uses its input sources to display the patient's blood pressure waveform as well as other patient data on display 15.

Control logic module 16 may comprise any adequate control means such as, but not limited to, a programmable gate array, a micro-controller or a control program in a host computer.

As detailed above, during therapy, indwelling pressure sensor 22 may change its calibration. This means that the signal that is produced is not a true indication of current arterial blood pressure.

In the present invention, control logic module 16 uses measurements from a calibrated secondary "reference" pressure signal source to calibrate the signal from the indwelling catheter 12. Since the secondary pressure sensor is external to the patient's body there is no constraint on its size. This allows for a pressure sensor construction that is more stable and accurate. Also, since an external transducer is re-usable, the expense associated with it and its calibration is more commercially acceptable.

In one embodiment of the present invention, the pressure sensor 22 is calibrated by using measurements of the "shuttle gas pressure" taken by pressure sensor 55. During the calibration process, the pneumatic system is configured and controlled so that the pressure within the IAB shuttle gas pneumatic circuit (shuttle gas pressure) closely approximates the patient's aortic pressure. This provides the means to calibrate pressure sensor 22 using measurements from pressure sensor 55. The details of this calibration process are discussed in detail below.

In another embodiment of the present invention, pressure transducer 22 is calibrated by using pressure measurements from a secondary pressure source, such as external AP input 66. External AP input 66 may comprise a signal produced, for example, by a blood pressure cuff system.

Figure 2:
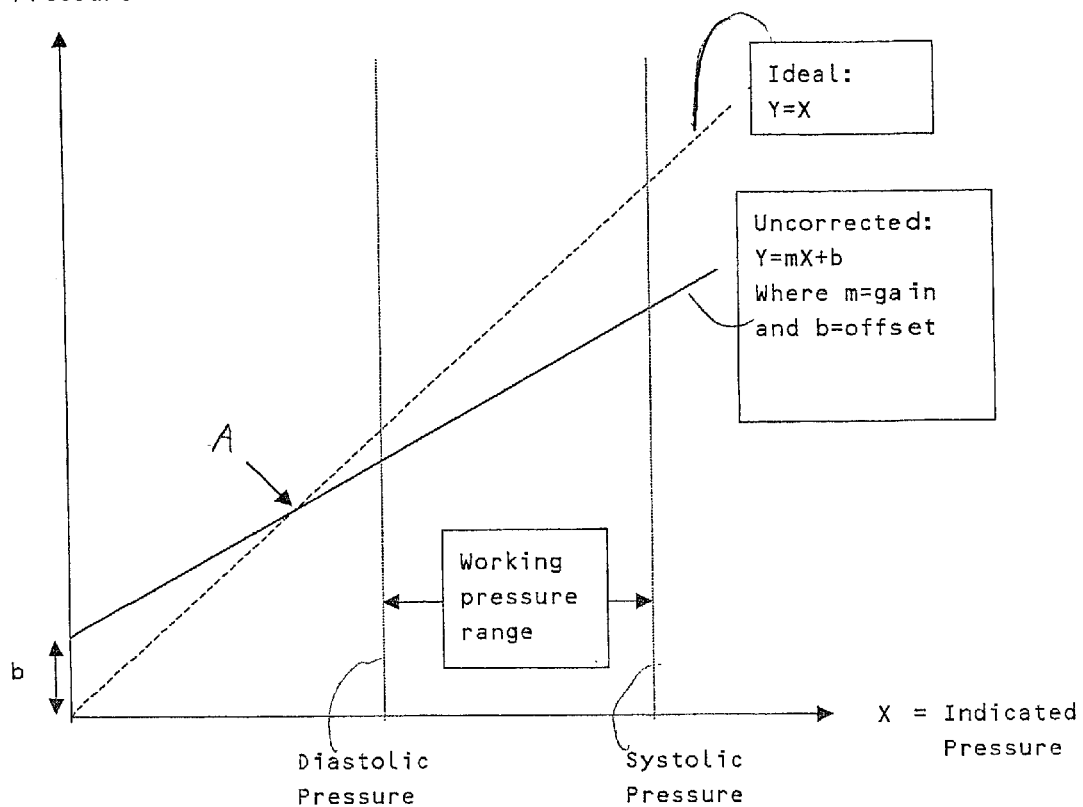
FIG. 2 is a plot of actual pressure versus indicated pressure with ideal and uncorrected plots.

FIG. 2 illustrates a solid line plot of actual pressure, on the Y-axis, versus indicated pressure, on the X-axis. The indicated pressure is the uncalibrated pressure outputted by pressure sensor 22 at a given point in time. The actual pressure (also referred to as true or reference pressure in the following examples) is the pressure assessed by a device not subject to drift, such as, but not limited to, shuttle gas pressure sensor 55 in the pneumatic drive module 14 or external pressure input 66.

The actual pressure, y, may have a linear functional relationship with respect to the indicated pressure, x. This functional relationship is shown in FIG. 2, using the equation, y=mx+b, where b is equal to the offset, i.e. the actual pressure at an indicated pressure of zero, and m is equal to the gain, i.e. the slope of the line which relates actual pressure to indicated pressure.

In FIG. 2 the transducer's "working pressure range" is shown as the range between diastolic pressure, represented by a vertical line labeled Diastolic Pressure, and systolic pressure, represented by a vertical line labeled Systolic Pressure. Mean pressure is also shown for reference. The ideal situation, where there is no error between the indicated pressures and actual pressures is shown as the "line of identity". This line is plotted using broken lines, and is labeled y=x.

Figure 3:
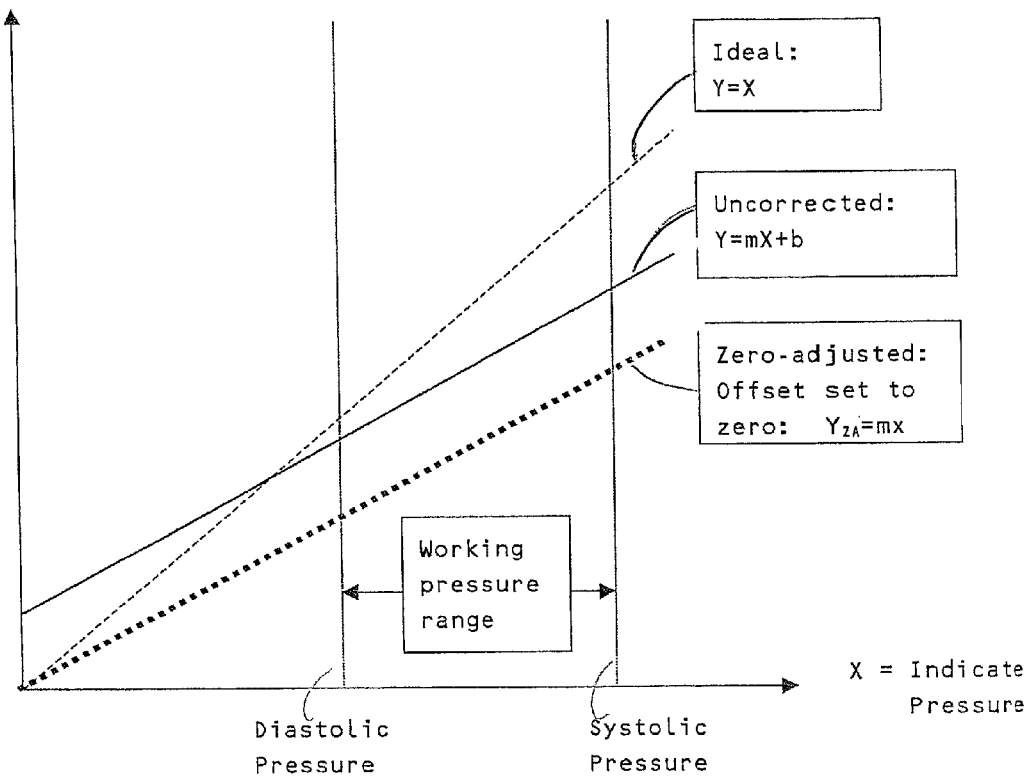
FIG. 3 is a plot of actual pressure versus indicated pressure with ideal and zero-adjusted plots.

FIG. 3 is a solid line plot illustrating the effect of offset error. For reference, the line of identity is also plotted. As illustrated, the offset of pressure sensor 22 is corrected and the gain is not.

Figure 4:
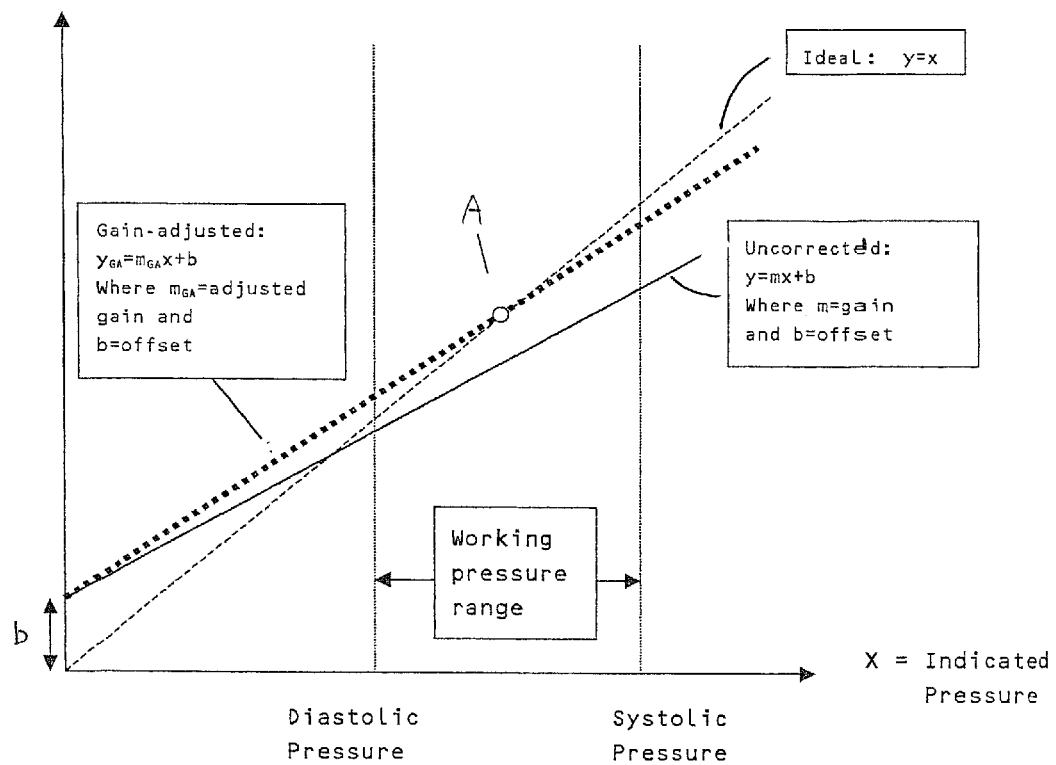
FIG. 4 is a plot of actual pressure versus indicated pressure with ideal and gain-adjusted plots.

FIG. 4 is a solid line plot of actual pressure versus gain adjusted and uncorrected pressures. The "line of identity" is plotted using broken lines and is labeled y=x. The gain adjusted pressure is plotted using a bolded broken line. Calibration at a single point is equivalent to forcing the adjusted output equation of pressure sensor 22 (bolded broken line) to intersect the line of identity at a single point, A, the chosen calibration pressure. If the calibration point is chosen to be at the patient's mean pressure, then the resultant errors for other pressures in the "working pressure" range is reduced.

If the calibration point is at atmospheric pressure, and there is an error in the transducer's gain or linearity, then due to mathematical "leverage", the likelihood of an error in the working pressure range is greatly increased.

In the system of the present invention, the calibration point is preferably chosen to be at the patient's mean pressure and the calibration process corrects both offset and gain at that pressure. The expected accuracy is perfect if the transducer is linear and it is greatly increased if the transducer is somewhat non-linear.

Using the methods and device detailed below, control logic module 16 of the present invention adjusts for both offset and gain. The uncalibrated aortic pressure signal, produced by catheter pressure sensor 22, is adjusted via use of a reference pressure measurement to produce an adjusted or corrected or calibrated pressure signal.

The reference pressure measurement is derived from the shuttle gas pressure sensor 55 in the pneumatic drive module 14 or, alternatively, it is derived from external AP input 66.

When shuttle gas pressure sensor 55 is used as the source for reference pressure readings, it is necessary to configure and initialize the IAB pneumatic circuit so that the pressure within it accurately reflects the patient's aortic pressure. This process, described in greater detail below, involves briefly suspending pumping, preferably for 3 to 5 heartbeats, during calibration. During these suspensions, balloon membrane 26 is continuously maintained in a partially inflated state while simultaneous pressure measurements are taken from catheter pressure sensor 22 and from shuttle gas pressure sensor 55. Note that if the reference source is external AP input 66 then suspension of pumping is unnecessary. Under proper conditions of IAB inflation, the pressure measured by the shuttle gas transducer will closely approximate the patient's aortic pressure, although its fidelity (frequency response) may be imperfect.

With regard to fidelity, the proposed method assumes that the reference pressure sensor, such as shuttle gas transducer 55 or external AP signal 55, provides an accurate measure of the patient's mean (DC) blood pressure, and an accurate measure of the low frequency components of the patient's pulse pressure. However, unlike some prior art devices, it does not assume or require that the shuttle gas pressure (or external source) accurately measures the higher frequency components (greater than approximately 6 Hz frequency response) of patient pressure. As will be discussed later, this is advantageous since the fidelity of the aortic pressure, as measured by the pressure sensor 55, is limited by the restrictive nature of IAB catheter 12 and the dead volume associated with the shuttle gas pneumatic circuit.

During calibration, simultaneous readings from catheter pressure sensor 22 and shuttle gas sensor 55 are used so that the effect of breathing or other artifactual sources will be in similar proportions in both the reference and catheter pressure sensor signals.

The calibration procedure preferably takes place during the routine purging of gas from IAB catheter 12, which occurs approximately every two hours. Hence, it has no impact on therapy.

Below the details of the calibration and correction processes are disclosed. For illustrative purposes during this discussion, a simple signal will be used as a proxy for patient blood pressure. Specifically, it is assumed that the input applied to pressure sensor 22 is the sum of a constant value $K_{dc}$ and a sinusoid of amplitude $K_{ac}$ at a frequency of $w_o$, i.e. $K_{ac}$ Sin $w_o$t. Therefore, if this input signal is perfectly reproduced by pressure sensor 22, then its output should be $K_{dc}+K_{ac}$ Sin $w_o$t.

Similarly, for purposes of illustration, pressure transducer 22 is assumed to be have a linear characteristic, of the form: y= mx+b which relates the measured signal, i.e. the input, to the indicated signal, i.e. the output.

Error in pressure sensor's 22 gain and offset results in errors in its output signal. In the case of our illustrative input signal, the resultant output with error is $(mK_{dc}+b)+mK_{ac}$ Sin $w_o$t.

The new constant term of the pressure sensor's 22 output is $mK_{dc}+b$. Thus, the error in the constant term of pressure sensor 22 output is due to both gain (m) and offset (b).

Error in the gain of pressure sensor 22 output also has the effect of changing the amplitude of the time varying sinusoid term from $K_{ac}$ to $mK_{ac}$; the error in amplitude in the varying sinusoid term, thus, being solely due to gain (m).

The goal of the calibration process of the present invention is to determine the values of pressure sensor 22's gain and offset errors. More specifically, the goal of the calibration process is to determine the values of m and b, and then use these values to produce an adjusted or calibrated pressure signal.

Accordingly, the proposed method has two distinct states: calibrate and run. In the calibrate state, the gain error (m) is determined first. This is then used as part of the computation for the offset error (b). In the run state, the adjusted pressure signal is produced using the values of m and b. Re-calibration of catheter pressure sensor 22 may be done on a periodic basis or when there is a predetermined change in mean pressure (operating point). Re-calibration at new operating points improves accuracy, particularly if non-linearity is present.

Figure 7:
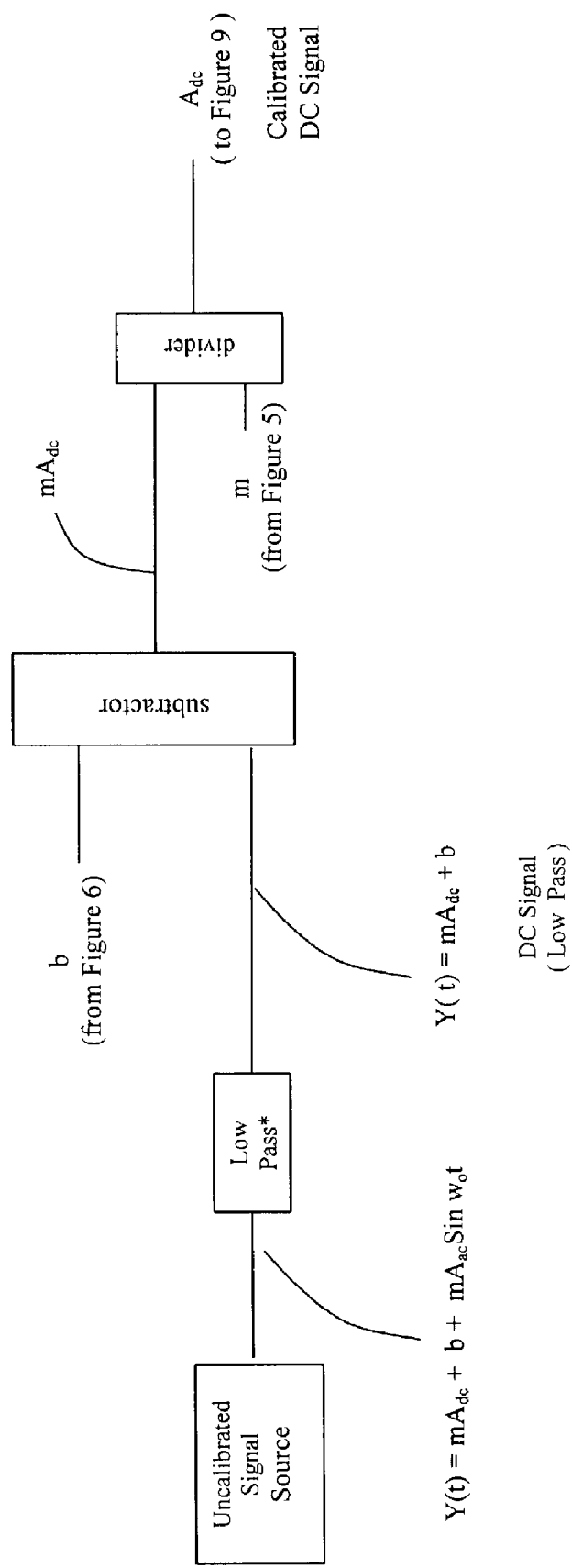
FIG. 7 is a high level block diagram detailing the computation of the calibrated DC in the run state.
Figure 8:
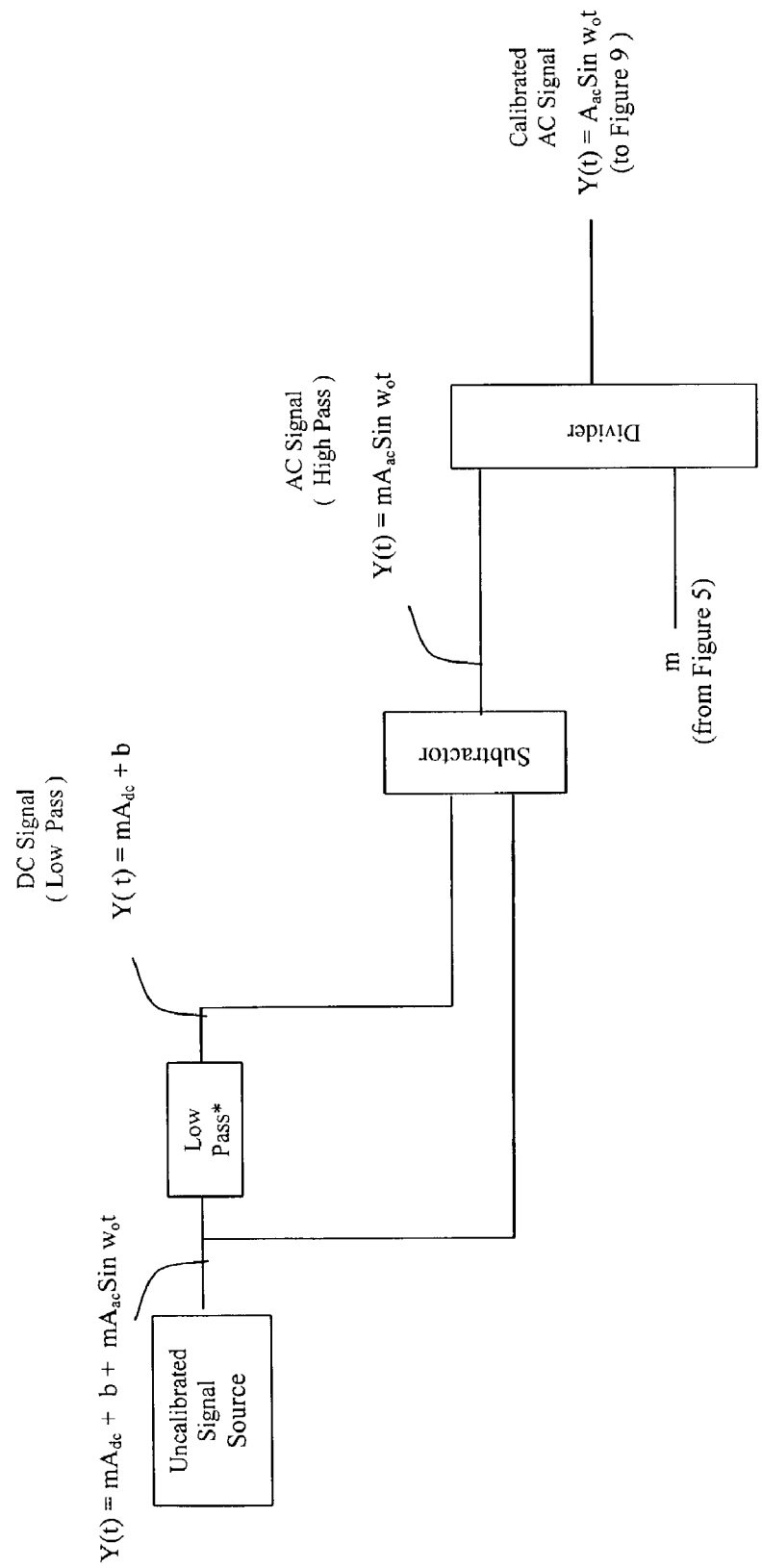
FIG. 8 is a high level block diagram detailing the computation of the calibrated AC signal in the run state.
Figure 9:
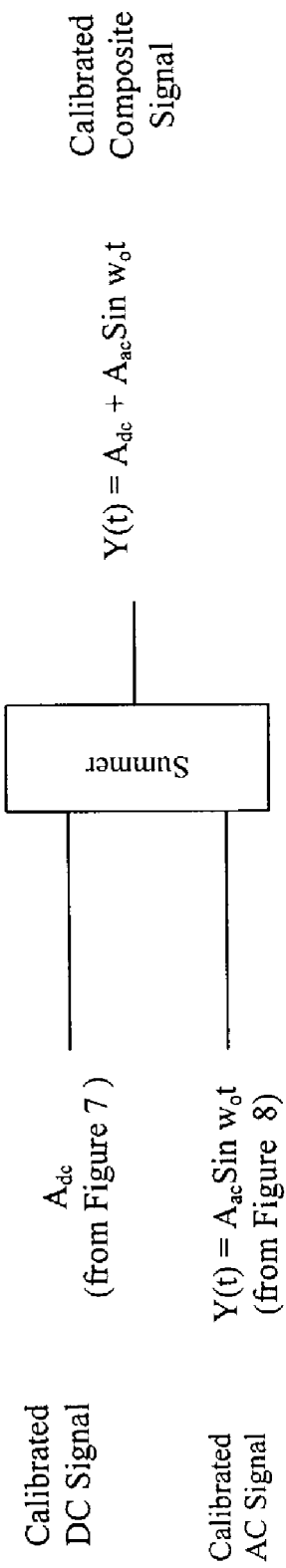
FIG. 9 is a high level block diagram detailing the computation of the calibrated composite signal in the run state.

FIG. 5–8 are high level block diagrams which detail the calibration process, i.e. the determination of the gain (m) and offset (b). In these diagrams, the amplitudes of the signals used in the calibration are designated using the letter "K" with the appropriate subscripts. This is done to differentiate these amplitudes from those occurring in the run state. FIG. 9 is a high level block diagram detailing the run state. The amplitudes of the signals in FIG. 9 are designated using the letter "A" with the appropriate subscripts.

Figure 5:
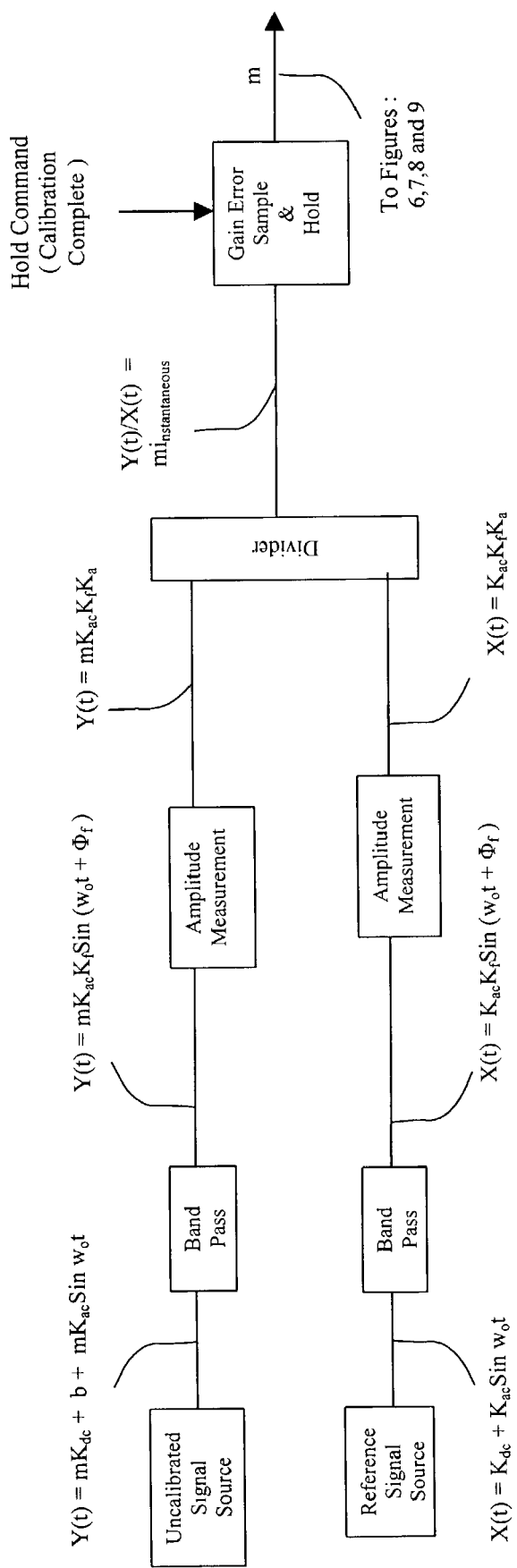
FIG. 5 is a high level block diagram detailing the computation of the gain (m) in the calibration state.
Figure 6:
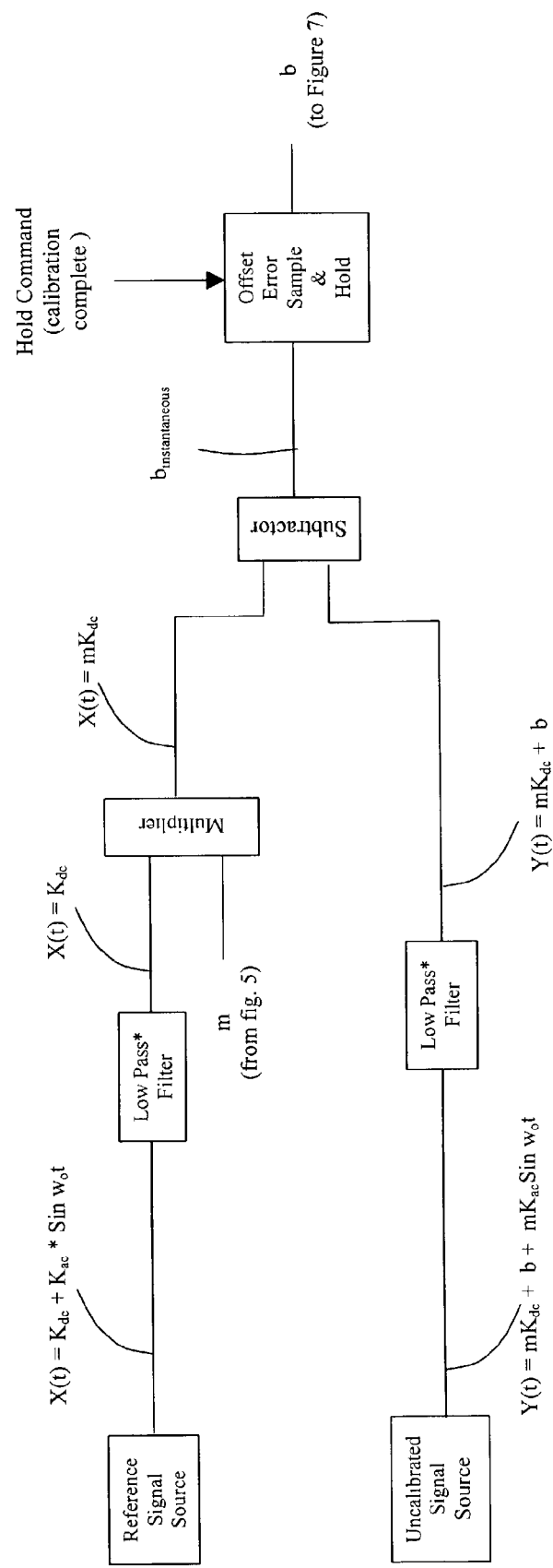
FIG. 6 is a high level block diagram detailing the computation of the offset (b) in the calibration state.

FIG. 5 is a high level block diagram detailing the determination of the catheter pressure sensor 22 gain error in the calibration state. FIG. 6 is a high level block diagram detailing the determination of the catheter pressure sensor 22 offset error (b) in the calibration state. FIG. 7 is a high level block diagram detailing the DC signal pathway of the indicated pressure signal in the run state. FIG. 8 is a high level block diagram detailing the AC signal pathway of the indicated pressure signal in the run state. FIG. 9 is a combination of the block diagrams in FIGS. 5 and 6. The upper portion of the block diagram is from FIG. 4 and the lower portion is from FIG. 5. The values of offset (b) and gain (m) outputted by the Sample and Hold devices of FIGS. 5 and 6 serve as inputs to the adder and divider devices in FIG. 9. The details of each block diagram are discussed below.

FIG. No. 5 details the determination of the catheter pressure sensor 22 gain error (m) in the calibration state. The computation follows the form of the definition of slope (gain). Specifically m=delta Y divided by delta X. In this illustrative case, the ratio of the amplitude of the sinusoids is used to compute slope. These sinusoids are extracted from the reference or actual pressure signal, labeled $X(t)=K_{dc}+K_{ac} \sin w_o t$, and uncalibrated or indicated pressure signal, labeled $Y(t)=mK_{dc}+b+mK_{ac} \sin w_o t$, by matched band pass filters. In practice, these filters extract the lower frequency AC components of the patient's aortic pulse blood pressure. The filters preferably exclude any frequency component not expected to be accurately measured by IAB membrane 26. The uncalibrated signal is converted to $Y(t)=mK_{ac} \sin w_o t$ and the reference signal is converted to $X(t)=K_{ac} \sin w_o t$. Then an index of amplitude of the sinusoids is computed, which is then output as: $Y(t)=mK_{ac}$ and $X(t)=K_{ac}$, respectively.

These indices of output amplitudes are then divided to yield slope (m). Because these terms are divided, any reasonable index of amplitude can be used in the computation, e.g. peak, RMS, average, etc. However, it is recommended that peak amplitude be avoided, since it may increase sensitivity to noise.

The average amplitude may be computed by integrating the absolute value of the respective signals over an integral or number of integral heartbeats. As noted above, any constant associated with the amplitude measurement process, or the band pass filters, is divided out by the computation of slope (m). This is illustrated in FIG. 5, wherein the factors $K_f$, $K_{ac}$ and $K_a$ are shown to be present and then divided out. These factors represent the scale factors of the filter and amplitude measurement processes. They are assumed to be identical for both signal pathways.

After the computation of slope (m) is complete, it is stored for use in the run state. The filters are preferably realized by computation, e.g. in a digital signal processor. This minimizes the introduction of error during the filtering process.

In particular, it is recommended that the filters used to extract the AC components are identical in their gain and phase characteristics. Because the filters are matched, their effects upon the amplitude and phase on the signals cancel out during the division process. Also, per the definition of slope, the filtering process is not required to yield a pure sinusoid.

Note that if there exists a significant time delay between the reference signal source and the uncalibrated signal source, then an error in the computation of slope can occur. Therefore, it is necessary to correct for the time delay prior to this computation. This can be done via buffering (storing) the reference and uncalibrated data and then re-aligning the data in time prior to the computation. Alternatively, prior to the computation of gain (m) the data can be implicitly re-aligned by following process: (1) Searching for the maxima peaks in the computation of amplitudes, e.g. search for the respective maxima from the RMS computations of amplitude, and then (2) Using these respective maxima in the computation of slope. The above process assumes that computation of amplitude is a continuous process, i.e. when calbrating, the amplitude measurement is updated at the sample rate, for example, of at least every 10 milliseconds.

FIG. 6 details the determination of the catheter pressure sensor 22 offset error (b) in the calibration state. Note that this computation requires the use of gain (m), stored in Sample and Hold by the calibration process shown in FIG. 5.

First, low pass filters are used on the reference and uncalibrated signals. For reasons indicated above, the filters are preferably matched. The filters extract the DC components of these signals, yielding $X(t)=K_{dc}$ and $Y(t)=mK_{dc}+b$. Next the low pass filtered reference signal, i.e. the DC component of the reference signal, is multiplied by the gain factor (m), yielding $X(t)=mK_{dc}$. This result is then subtracted from low pass filtered uncalibrated signal, i.e. the DC component of the uncalibrated signal, yielding the offset (b). This value is then stored in a Sample and Hold for use during the run state.

The low pass filters accurately determine the DC or mean value of their respective pressure waveforms. The mathematical basis for this method is the Fourier transform. The Fourier transform computes an equivalent series to a given function. The equivalent series is the sum of a DC term (mean of the input function) and the sum of harmonically related sinusoids and/or co-sinusoids. The filtering process severely reduces the amplitude of these sinusoids and thereby extracts the mean/DC term.

FIGS. 7–9 include block diagrams detailing the run state. When in the run state, the uncalibrated signal from the catheter pressure sensor 22 is continuously low pass filtered. The filtering allows for the creation of two separate signals, AC and DC. These signals are individually re-calibrated and then summed to regenerate a calibrated aortic pressure waveform. Re-calibration is accomplished by application of the offset and gain correction constants, as stored in FIGS. 5 and 6. As noted above, the signal shuttle gas pressure signal is not needed or used while in the run state.

In FIGS. 7–9 the amplitudes of the AC and DC components of the uncalibrated signal are indicated by use of letter "A" with the appropriate subscripts. This is done to differentiate run state signal amplitudes from calibrate signal amplitudes. For example, if the output is perfectly calibrated then it should be:

$$A_{dc}+A_{ac} \sin w_o t.$$

FIG. 7 details the DC signal pathway. In this pathway, the indicated or uncalibrated signal from the catheter pressure sensor 22 is continuously low pass filtered to extract its DC components. The output of the filter is $Y(t)=mA_{dc}+b$. The offset calibration constant, b, taken from the Sample and Hold device in FIG. 3, is then continuously subtracted from the filtered DC signal. The result, $mA_{dc}$, is continuously divided by the gain (m), stored as shown in FIG. 5, which yields the corrected DC signal, $A_{dc}$.

FIG. 8 details the AC signal pathway and the production of corrected AC signal used in the summation above. The output of the low pass filter, $Y(t)=mA_{dc}+b$, is subtracted from the indicated catheter pressure sensor 22 signal, yielding $Y(t)=mA_{ac} \sin w_o t$. The subtractor excludes the DC component and passes all AC components. This subtraction process yields the effect of matched high pass filters.

Note that the above disclosed filtering creates symmetric low pass and high pass versions of the pressure signal, such that the original signal is perfectly regenerated when the high and low pass signals are summed together. This symmetry is used when the system is in the "RUN" state, wherein the composite calibrated signal is generated by summation of the high and low pass signals.

The signal, $Y(t)=mA_{ac} \sin w_o t$, is then divided by the gain correction constant (m), which was stored in FIG. 5, thereby yielding a calibrated AC signal.

FIG. 9 details the creation of the composite calibrated signal. This signal is created by summing the calibrated AC signal $A_{ac} \sin w_o t$, as determined by the block diagram in FIG. 8, and DC signal $A_{dc}$, as determined by the block diagram in FIG. 7.

It is important to understand the distinction in filtering that is done in the calibrate and run states. In the calibrate state, the reference source and uncalibrated source may be filtered aggressively to assure accurate determination of the gain slope "m". In the run state, the calibration coefficients, m and b are known. Filters are used to separate and recalibrate the signal from catheter pressure sensor 22. These filters are not intended to reduce the fidelity or frequency content of the signal from catheter pressure sensor 22.

Note in FIGS. 5–9 one may optionally include identical median filters prior or to the left of the low pass filters. Median filters eliminate impulse noise, and thus, prevent erroneous excitation of the low pass filter's impulse response.

It is understood that the calibration function can be realized as a software program or via use of analog and/or digital circuitry. For example, in FIGS. 5 and 6,the band pass filter(s) can be realized by placing a low pass and high pass filter in series. This provides flexibility in the control of the filter's characteristics. Commonly, these filters are realized by operational amplifiers configured in the Sallen-Key configuration. Other configurations, such as state variable may be used as well. Similarly, in FIGS. 7–9, the low pass filter(s) can be realized via operational amplifiers configured in the Sallen-Key configuration. Other configurations, such as state variable will work as well.

In FIG. 5, the amplitude measurement function can be realized by a specialized integrated circuit, such as a True RMS to DC (Root Mean Square Converter). This device continuously computes the true RMS value of the signal applied to its input and converts it to a proportionate DC value. Furthermore, the functions of addition and subtraction are readily implemented using operational amplifiers. The remaining functions of multiplication, division and sample and hold, are best realized via computation. However, specialized integrated circuits are available for these functions as well.

Note that because the time duration of the "hold" interval can be on the order of minutes or hours, the sample and hold function is preferably realized by digitizing the value and storing the result. To convert digitized data back into analog forms, a Digital to Analog Converter is used.

Figure 13:
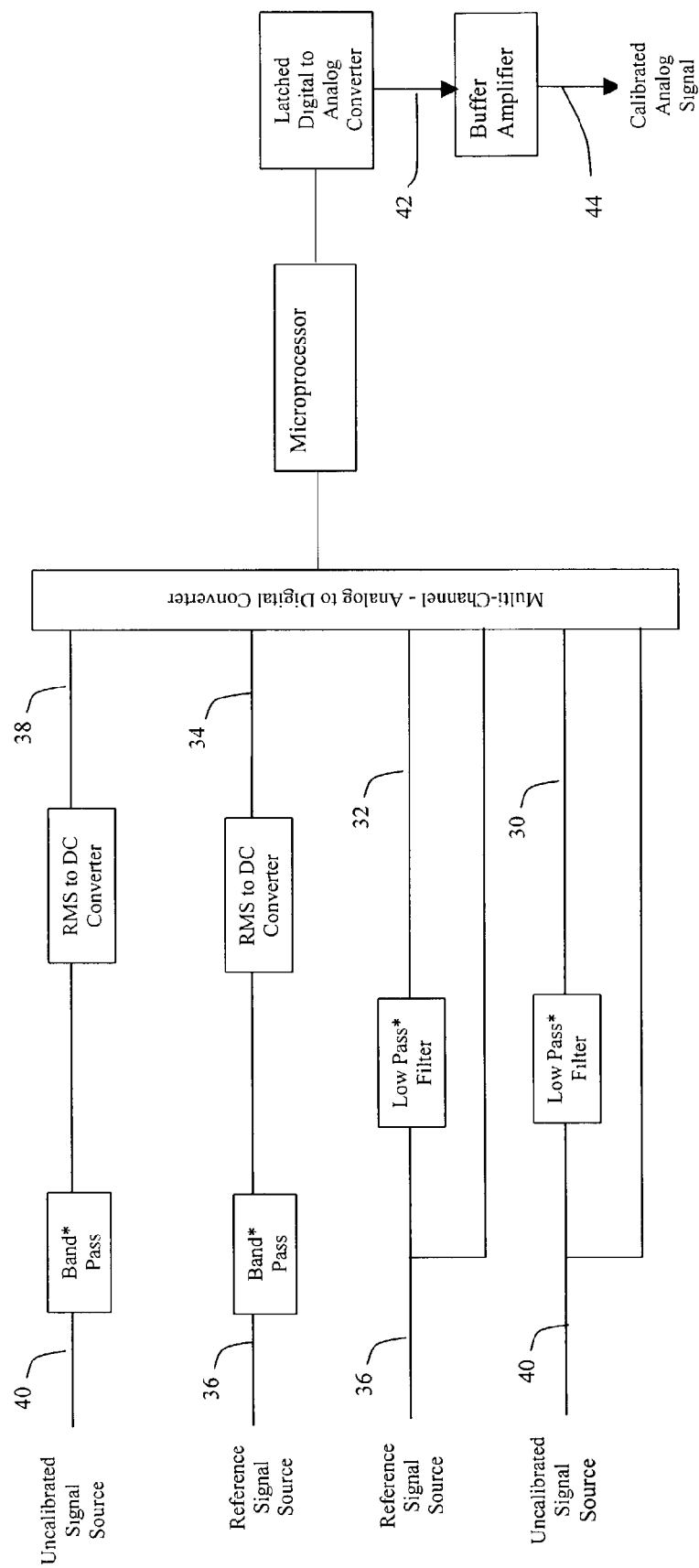
FIG. 13 is a block diagram of an alternate implementation of the present invention using a microprocessor.

FIG. 13 shows a hybrid configuration, which uses a combination of computation and dedicated circuitry. Numerous other configurations can be devised which are functionally equivalent. An Analog to Digital Converter has 6 inputs, an Uncalibrated Signal 40, a Modified Uncalibrated Signal 38, a Second Modified Uncalibrated Signal 30, a Reference Signal 36, a Modified Reference Signal 34 and a Second Modified Reference Signal 32. The Modified Uncalibrated Signal 38 comprises the Uncalibrated Signal 40 after it has passed through a Band Pass Filter and a RMS to DC Converter. The Second Modified Uncalibrated Signal 30 comprises the Uncalibrated Signal 40 after it has passed through a Low Pass Filter. The Modified Reference Signal 34 comprises the Reference Signal 36 after it has passed through a Band Pass Filter and a RMS to DC Converter. The Second Modified Reference Signal 32 comprises the Reference Signal 36 after it has passed through a Low Pass Filter. The digitized output of the Analog to Digital converter is then passed into a Microprocessor, which outputs a digitized calibrated signal 42. Digitized calibrated signal 42 is then passed through a Buffer Amplifier to produce a Calibrated Analog Signal 44.

Acquiring the Secondary Pressure Signal

As indicated above, in order to measure aortic pressure across balloon membrane 26, pumping is briefly suspended, preferably for 3 to 5 heartbeats. During these suspensions, balloon membrane 26 is maintained in a partially inflated state. Then, simultaneous pressure measurements are taken from the catheter pressure sensor 22 and the shuttle gas pressure 55 or another external pressure 66. Using methods described above, the shuttle gas pressure measurements are used as a reference for correction (re-calibration) of pressure sensor 22's measurements, i.e. for correction of the uncalibrated or indicated pressure signal.

The disclosed invention defines the necessary conditions for measurement of aortic pressure via partial IAB inflation. The invention also recognizes that the fidelity of this measurement is limited and compensates for it. Further, the invention recognizes that there exists an optimum value for partial IAB inflation that maximizes the fidelity of the measured aortic pressure waveform. The invention also recognizes the negative impact of pneumatic dead volume on waveform fidelity and proposes methods to improve it.

In order to be a valid source for reference pressure, the balloon membrane 26 must be "properly" under inflated. For example, consider the case where balloon membrane 26 is fully inflated. Full inflation can only occur if the pressure within balloon membrane 26 exceeds patient blood pressure at all times. In this case, the IAB membrane is completely tensed. Therefore, the pressure within balloon membrane 26 is constant and is not correlated with patient blood pressure. Consider the opposite case wherein balloon membrane 26 is fully deflated. Full deflation can only occur if the pressure within balloon membrane 26 is less than patient blood pressure at all times. In this case, balloon membrane 26 is completely flattened. The pressure within balloon membrane 26 is constant and is not correlated with patient blood pressure. Thus, full inflation and full deflation states are not considered "properly" under inflated.

There also exists a state of partial inflation in which the pressure waveform is clipped or distorted because the instantaneous value of the pressure is sufficient to momentarily permit full IAB inflation or momentarily permit full IAB deflation. Both of these situations can lead to distorted and clipped blood pressure waveforms.

Finally, there exists a specific degree of under inflation, the "optimum inflation", wherein the balloon's pressure best approximates the patient's blood pressure. In this case, the pressure within the IAB is nominally identical to patient blood pressure. Since the calibration process relies on proper balloon membrane 26 inflation volume, a method for selecting the optimum inflation volume is needed.

As indicated above, when balloon membrane 26 is over inflated or not "properly" under inflated, the pressure waveform measured across balloon membrane 26 is distorted or clipped. Clipping is a non-linear process, when it occurs, the harmonic content of the signal increases. Comparison of the signals produced by catheter pressure sensor 22 and shuttle gas pressure sensor 55 provides a means for detection of improper balloon membrane volume.

Control logic module 16 adds small amounts of gas to the shuttle gas pneumatic circuit. This additional gas influences the displaced volume of IAB balloon membrane 26. Control logic module 16 then runs the calibration process and computes an index of distortion, for the duration of one or more heartbeats. The term "index of distortion" is a measure of the increase in distortion and harmonic energy in the waveform measured by shuttle gas pressure transducer 55. The intent is to detect and quantify signal distortion.

Control logic module 16 then adds more gas, repeats the curve fit and computes the new index of distortion. This is continued until the index of distortion is minimized or until a predetermined maximum safe balloon membrane 26 volume is reached. This process produces an ideal balloon membrane 26 inflation volume for the purpose of measuring pressure across balloon membrane 26. The curve fit associated with the least distortion is then taken to be the best, and it is used thereafter in the run state for calibration.

One example of a normalized distortion index is the ratio of the RMS values of the respective pressure signals. Another index is the correlation between the reference AC waveform and the shuttle gas AC waveform. When the correlation between these signals is maximized, then they are "most alike", i.e. the shuttle gas pressure waveform is least distorted when it is most correlated with the reference.

Another way to detect distortion is to use a higher order calibration curve fit than is needed. Distortion could be detected by comparison of the curve fits at each IAB inflation volume. When distortion is present, the coefficients are expected to change as a consequence of the impact of IAB signal's distortion on the curve fit. In particular, it is likely that the magnitude of the second order and higher order terms would increase in the presence of IAB distortion.

Another way to detect distortion is to compare the Fourier transforms of the signals from pressure sensor 22 and as measured across balloon membrane 26. When distortion occurs, new harmonics will appear in the transform of the signal detected by IAB sensor 55 transform relative to the transform of the signal detected by pressure sensor 22. Also, the degree of inflation can be determined by examining pressure measurements taken across the balloon membrane at different inflations levels and selecting the one that produces the simplest frequency spectra, i.e. the least number of harmonics.

Minimization of Dead Volume

Dead volume and catheter resistance work in concert to attenuate the fast moving features of a patient's blood pressure waveform. While catheter resistance can be reduced by increasing the size of catheter 12, for clinical reasons, including reduction of the incidence of limb ischemia, it is preferable to keep the catheter 12's diameter small. Consequently, in order to maintain waveform fidelity it is necessary to minimize dead volume.

Reducing the dead volume associated with the IAB when calibrating has four benefits. First, it increases the frequency response of the IAB balloon membrane as a monitoring device. Second, it extends the range of usable IAB volumes, i.e. a larger range of under inflation, wherein no clipping occurs. Third, it increases the dynamic range of the monitoring function, i.e. when dead volume is reduced a clipping will occur at higher pulse (peak to peak) pressure. Fourth, it allows the use of smaller IABs, i.e. IAB's with less volume.

If a small IAB catheter 12 is used to sense pressure, when a large amount of dead volume is present, then the measured waveform may be clipped because balloon membrane 26 may fully or partially deflate or inflate during changes in patient blood pressure.

Dead volume can be reduced by a number of means. The dead volume associated with extension catheter 46, a tube used to connect the IAB catheter to the IABP (not shown in FIG. 1, but shown in FIGS. 10–12), can be reduced by reducing its length and diameter. However, clinical and practical considerations limit the magnitude of these changes.

Figure 10:
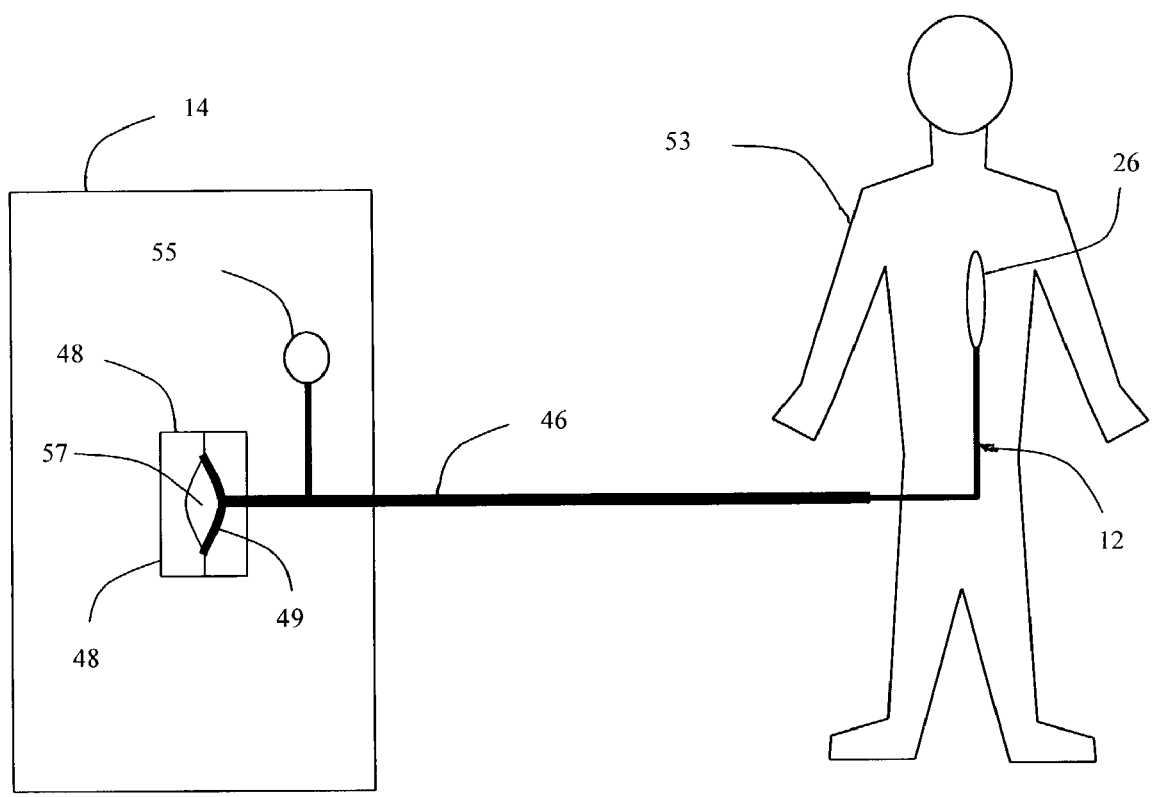
FIG. 10 is a block diagram of the IAB catheter inserted into a patient on one end and connected to the pneumatic drive module, with isolator in a forward position, on the other.
Figure 11:
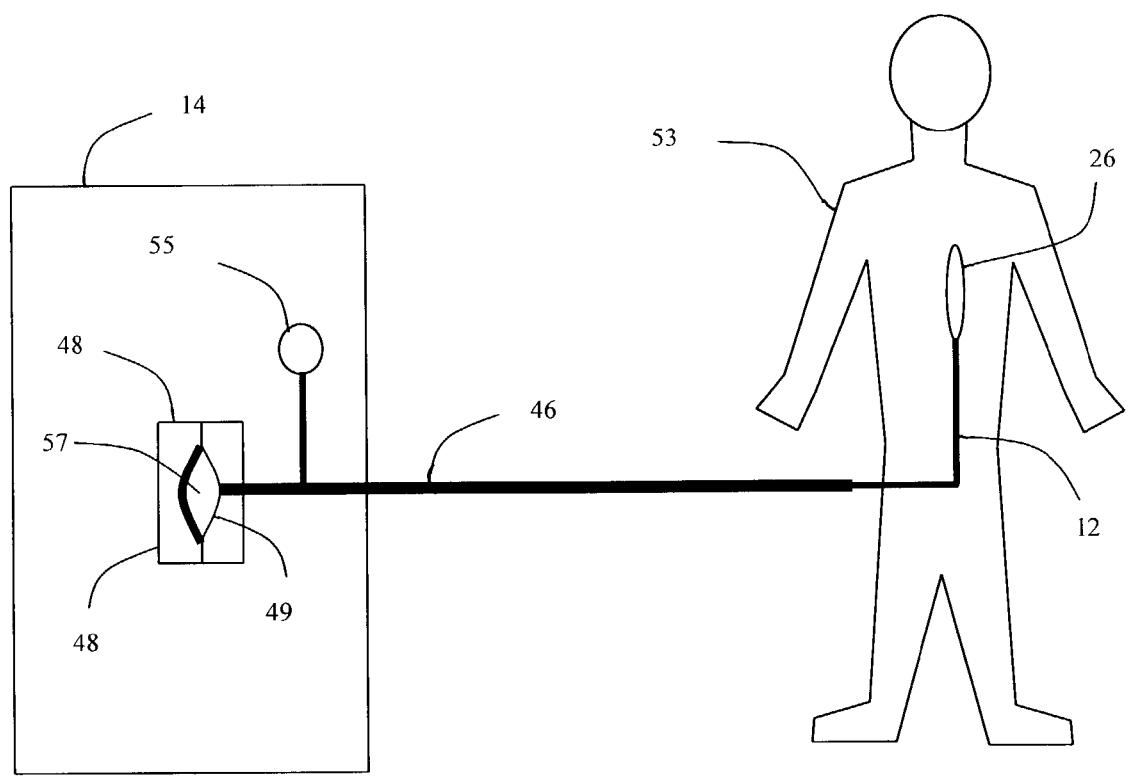
FIG. 11 is a block diagram of the IAB catheter inserted into a patient on one end and connected to the pneumatic drive module, with isolator in a rearward position, on the other.
Figure 12:
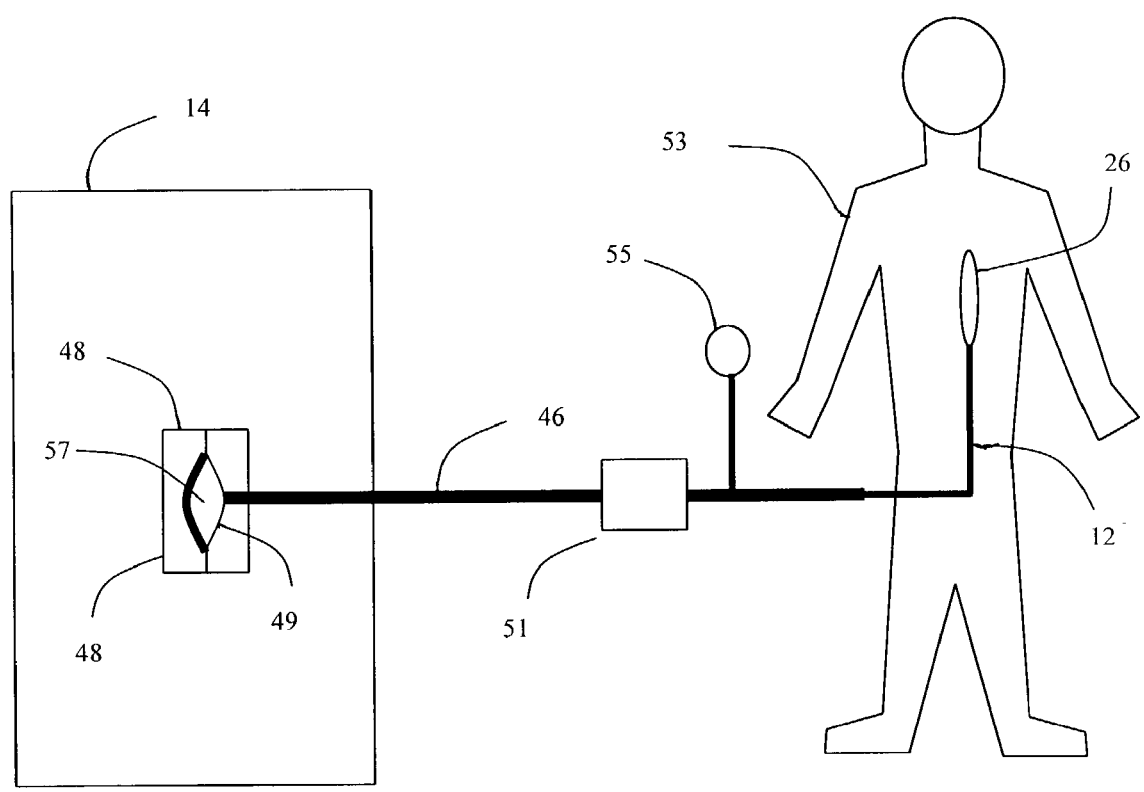
FIG. 12 is a block diagram of FIG. 11 including a series valve connected to the IAB catheter.

In FIGS. 10–12 IAB catheter 12 is inserted in a patient 53. Extension catheter 46 is connected on one end to IAB catheter 12 and on an opposite end to an isolator 48 in pneumatic drive module 14. Isolator 48 preferably comprises a membrane 49 that shifts from a forward position/convex configuration, as illustrated in FIG. 10, to rearward position/concave configuration, as illustrated in FIG. 11 during normal pump/pneumatic drive module 14 operation. Membrane 49 is enclosed in a cavity 57 that communicates with extension catheter 46. Dead volume in pneumatic drive module 14 may be minimized by assuring that patient isolator 48's volume is minimized during the calibration process. This may be achieved by shifting isolator membrane 49 to a fully forward position/convex orientation during calibration, as in FIG. 10.

Alternatively, during calibration, the dead volume in pneumatic drive module 14 and extension catheter 46 may be temporarily isolated from IAB catheter 12 and pressure sensor 55 via a series valve 51, as in FIG. 12.

In yet another embodiment, IAB catheter 12 may have a separate gas lumen for the purpose of sensing pressure in IAB catheter 12, such that the pressure drop in indwelling IAB catheter 12 is not seen by the separate sensing lumen. Such lumen should have an area that is smaller than the gas passage area of IAB catheter 12. This IAB configuration can be used in conjunction with the measures cited above to maximize fidelity.

As many apparently widely different embodiments of the present invention can be made without departing from the spirit and scope thereof, it is to be understood that the invention is not limited to the specific embodiments thereof except as defined in the appended claims.

What is claimed is:

1. A method for calibrating a catheter mounted pressure sensor, said sensor outputting an uncalibrated source signal having a constant signal component and a time varying signal component, comprising the steps of (a) producing a calibrated time varying signal and a calibrated constant signal by separately calibrating the constant signal component and the time varying signal component; (b) adding the calibrated constant and time varying signals together to produce a calibrated source signal.

2. A method for calibrating a catheter mounted pressure sensor, said sensor outputting an uncalibrated source signal comprising a constant signal component and a time varying signal component, said method comprising the steps of (a) calculating a gain correction factor; (b) calculating an offset correction; (c) producing a calibrated time varying signal by calibrating the time varying signal component; (d) producing a calibrated constant signal by calibrating the constant signal; and (e) adding the calibrated constant and time varying signals together to produce a calibrated source signal.

3. The method as claimed in claim 2 wherein the gain correction factor is calculated by dividing the amplitude of the time varying component of the uncalibrated source signal by the amplitude of the time varying component of a reference source signal, said reference source signal not being prone to signal drift.

4. The method as claimed in claim 2 wherein the amplitude of the time varying component of the uncalibrated source signal is produced by band pass filtering the uncalibrated source signal and wherein the amplitude of the time varying component of the reference source signal is produced by band pass filtering the reference source signal.

5. The method as claimed in claim 2 wherein the offset correction is calculated by subtracting (a) the constant component of the uncalibrated signal source and (b) the constant component of the reference signal source multiplied by the gain correction factor.

6. The method as claimed in claim 2 wherein the calibrated time varying signal component is produced by (a) subtracting the uncalibrated source signal from the constant component of the uncalibrated source signal to produce a high pass time varying signal; and (b) dividing the high pass time varying signal by the gain correction factor.

7. The method as claimed in claim 2 wherein the calibrated time varying signal component is produced by (a) subtracting the uncalibrated source signal from a low pass filtered uncalibrated source signal to produce a high pass time varying signal and (b) dividing the high pass time varying signal by the gain correction factor.

8. The method as claimed in claim 2 wherein the calibrated constant signal component is produced by (a) subtracting the offset correction from the constant component of the uncalibrated source signal and (b) dividing the signal resulting from step(a) by the gain correction factor.

9. The method as claimed in claim 2 wherein the calibrated constant signal component is produced by (a) subtracting the offset correction from a low pass filtered uncalibrated source signal and (b) dividing the signal resulting from step(a) by the gain correction factor.

10. The method as claimed in claim 2 wherein the gain correction factor and offset correction are recalculated on a periodic basis.

11. The method as claimed in claim 2 wherein the gain correction factor and offset correction are recalculated when an amplitude of the calibrated source signal falls out of a predetermined range.

12. The method as claimed in claim 1 wherein the calibrated constant signal component and the calibrated time varying signal component are calibrated using a reference source signal not being prone to signal drift.

13. The method as claimed in claims 3 or 12 wherein the pressure sensor is mounted on a catheter terminating in a balloon membrane and wherein the reference source signal is obtained by measuring pressure across the balloon membrane in a partially inflated state.

14. The method as claimed in claims 3 or 12 wherein the pressure sensor is mounted on a catheter terminating in a balloon membrane and wherein the reference source signal is obtained by measuring pressure across the balloon membrane in a partially inflated state, the degree of inflation being determined by comparing signal from the catheter mounted pressure sensor and the signal obtained from measurements across the balloon membrane.

15. The method as claimed in claims 3 or 12 wherein the pressure sensor is mounted on a catheter terminating in a balloon membrane and wherein the reference source signal is obtained by measuring pressure across the balloon membrane in a partially inflated state, the degree of inflation being determined by comparing the Fourier transform of the signal from the catheter mounted pressure sensor and the Fourier transform of the signal obtained from measurements across the balloon membrane.

16. The method as claimed in claims 3 or 12 wherein the pressure sensor is mounted on a catheter terminating in a balloon membrane and wherein the reference source signal is obtained by measuring pressure across the balloon membrane in a partially inflated state, the degree of inflation being determined by comparing for a plurality of inflation levels of the balloon membrane the root mean square values of measurements taken from the catheter mounted pressure sensor and the root means square values of measurements corresponding in time from across the balloon membrane.

17. The method as claimed in claims 3 or 12 wherein the pressure sensor is mounted on a catheter connected on one end to a balloon membrane and on an opposite end to an isolator chamber, said isolator chamber comprising a membrane, said membrane splitting the isolator chamber into a forward chamber and a rearward chamber, said forward chamber being in communication with a lumen defined by the catheter, the membrane having a forward configuration and a rearward configuration, when the membrane is in the forward configuration the volume of the forward chamber is smaller than it is when the membrane is in the rearward configuration, the reference source signal is obtained by measuring pressure across the balloon membrane in a partially inflated state while the membrane is in the forward configuration.

18. The method as claimed in claims 3 or 12 wherein the pressure sensor is mounted on a catheter connected on one end to a balloon membrane and on an opposite end to pumping means, said catheter having a valve connected to it and a pressure sensor connected to it between the valve and the balloon membrane, the reference source signal is obtained by measuring pressure across the balloon membrane in a partially inflated state via the pressure sensor while the valve is closed.

19. The method as claimed in claims 3 or 12 wherein the pressure sensor is mounted on a catheter connected on one end to a balloon membrane and on an opposite end to pumping means, said catheter defining a shuttle gas lumen and a pressure sensing lumen, the reference source signal is obtained by measuring pressure across the balloon membrane in a partially inflated state via the pressure sensing lumen.

20. The method as claimed in claims 3 or 12 wherein the pressure sensor is mounted on a catheter terminating in a balloon membrane and wherein the reference source signal is obtained by measuring pressure across the balloon membrane in a partially inflated state, the degree of inflation being determined by examining pressure measurements taken across the balloon membrane at different inflations levels and selecting the one that produces the simplest frequency spectra.

21. The method as claimed in claim 3 wherein prior to dividing the amplitude of the time varying component of the uncalibrated source signal by the amplitude of the time varying component of a reference source signal the time varying component of the uncalibrated source signal and the time varying component of the reference source signal are time aligned.

* * * * *